United States Patent [19]

Quinn

[11] Patent Number: 5,201,723
[45] Date of Patent: Apr. 13, 1993

[54] INCLINED SIDE HOLES IN THE DISTAL END OF A CATHETER

[75] Inventor: David M. Quinn, Miami, Fla.

[73] Assignee: Cordis Corporation, Miami Lakes, Fla.

[21] Appl. No.: 750,498

[22] Filed: Aug. 27, 1991

[51] Int. Cl.$^5$ .................... A61M 5/00; A61M 25/00
[52] U.S. Cl. .................... 604/264; 604/280; 604/282
[58] Field of Search .............. 604/264, 280, 281-282; 128/656-658, 772

[56] References Cited

U.S. PATENT DOCUMENTS

| | | | |
|---|---|---|---|
| 4,639,252 | 1/1987 | Kelly et al. | 604/282 |
| 4,801,297 | 1/1989 | Mueller | 604/264 |
| 4,863,441 | 9/1989 | Lindsay et al. | 604/264 |
| 5,037,403 | 8/1991 | Garcia | 604/280 |
| 5,061,257 | 10/1991 | Martinez et al. | 604/282 |
| 5,069,673 | 12/1991 | Shwab | 604/281 |

Primary Examiner—C. Fred Rosenbaum
Assistant Examiner—Ronald K. Stright, Jr.
Attorney, Agent, or Firm—Henry W. Collins; Thomas R. Vigil

[57] ABSTRACT

A catheter for uses in an angioplasty system comprising a tubular body with a proximal end, a distal end and a distal end portion and having a plurality of holes in and along opposite sides of the distal end portion. Each hole has an elongate shape and a center and the centers of the holes are located on an imaginary line parallel to the longitudinal axis of the catheter. Each elongate hole is inclined not less than 30 degrees and not more than 60 degrees to the imaginary line and each elongate hole on one side of the catheter is inclined upwardly or downwardly of the imaginary line and each opposite side hole on the other side of the catheter is inclined upwardly or downwardly relative to the imaginary line so that opposed holes form an X.

10 Claims, 2 Drawing Sheets

INCLINED SIDE HOLES IN THE DISTAL END OF A CATHETER

BACKGROUND OF THE INVENTION

1. Field of the invention.

The present invention relates to a catheter, such as a pigtail catheter widely used today by angiographers for inserting into the ventricle for the treatment of patients with aortic stenosis. They are easy to place, minimize intimal trauma and have improved stability. However, even with a standard pigtail catheter, kinking of the tubular distal end of the catheter, especially kinking of the performed curved pigtail, is often incurred during useage. The catheter of the present invention avoids kinking by the provision of inclined side holes punched into the tubular distal end of the catheter.

2. Description of the Related Art.

The standard pigtail catheters used nowadays, have up to twelve elliptical side holes in the distal end of the tubular body of the catheter. The elliptical side holes are located within the tubular body as close as possible to the performed curved pigtail. The side holes are arranged in three sets of four side holes, whereby the four side holes are equally distributed on the perimeter and the three sets of side holes are located next to each other. All elliptical side holes are arranged co-axial to the longitudinal axis of the catheter. This arrangement allows rapid injections of contrast media into the ventricle with minimal myocardial irritation.

As described more specifically hereinafter, the present invention differs significantly from the standard pigtail catheter by the provision of inclined side holes in the catheter wall.

SUMMARY OF THE INVENTION

According to the invention there is provided a catheter for use in an angioplasty system. The catheter comprises a tubular body with a proximal end, a distal end and a distal end portion having a plurality of holes in and along opposite sides of the distal end portion. Each hole has an elongate shape and is centered and axially aligned with the center of the hole on the opposite side of the distal end portion. The center of the holes are located on an imaginary line parallel to the longitudinal axis of the catheter. Each elongate hole is inclined not less than 30° and not more than 60° upwardly or downwardly to the imaginary line. Further, each elongate hole on one side of the catheter is inclined upwardly or downwardly of the imaginary line and each opposite side hole on the other side of the catheter is inclined to the imaginary line at a different angle than the aligned hole on the one side of the catheter so that each pair of opposed holes form an X.

Also according to the invention there is provided a catheter comprising a tubular body having a proximal end, a distal end and a distal end portion having holes located in the distal end portion in and along opposite sides of the distal end portion. Each hole has an elongate shape, the center being axially aligned with the center of the hole on the opposite side of the distal end portion with the centers of the holes being located on an imaginary line parallel to the longitudinal axis of the tubular body and each hole being inclined upwardly or downwardly relative to an imaginary line parallel to the longitudinal axis of the tubular body and the holes on one side being inclined to the imaginary line at a different angle than the holes on the other side such that opposed holes form an X for minimizing kinking of the tubular body when it is bent.

DESCRIPTION OF THE PREFERRED EMBODIMENT

Figure 1:
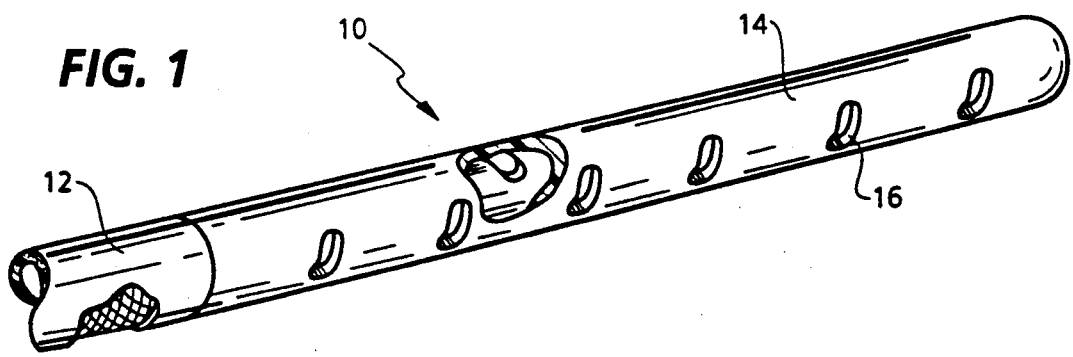
FIG. 1 is a perspective view of a distal end of a catheter with parts broken away and shows side holes within an extruded elastomeric tip of the catheter.

Referring now to the drawings in greater detail, there is illustrated in FIGS. 1-7, a catheter 10 having a tubular braided body 12 with a molded or extruded elastomeric tip 14 fused thereon. The elastomeric tip 14 can be a preformed curved tip for use as a pigtail catheter in an angioplasty system (not illustrated).

Catheters of this type are widely used today by angiographers for inserting and traversing human blood vessels for the treatment of aortic stenosis patients. The pigtail catheters in particular are used by angiographers for inserting into the ventricle, because they are easy to place, minimize intimal trauma, and have improved stability.

Figure 3:
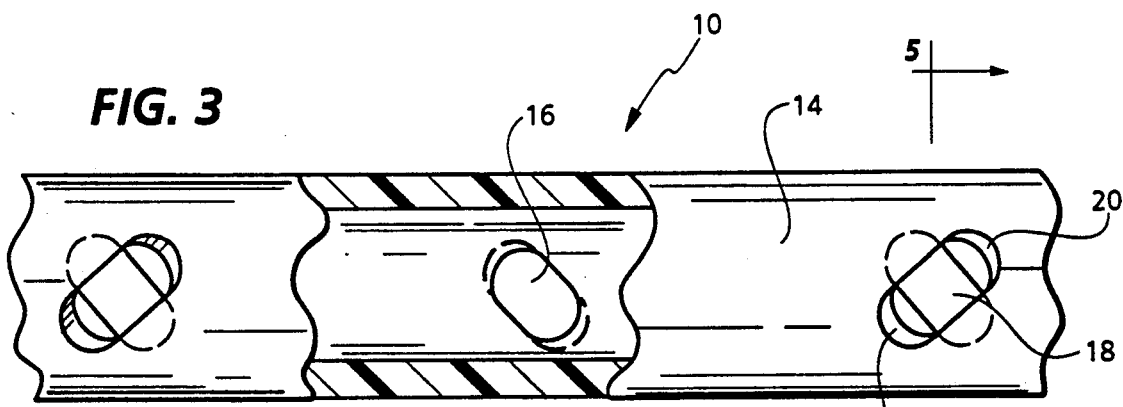
FIG. 3 is a side view of the distal end of the catheter shown in FIG. 1 with parts broken away.
Figure 5:
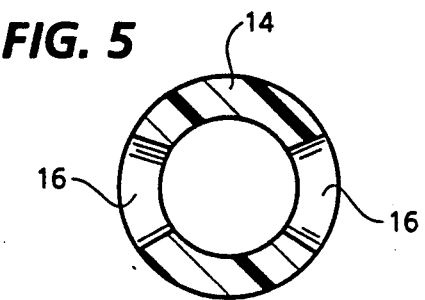
FIG. 5 is a sectional view of the distal end of the catheter of FIG. 1 and is taken along line 5—5 of FIG. 3.

A first embodiment of a catheter constructed according to the teachings of the present invention is shown in FIGS. 1, 3 and 5, wherein up to twelve side holes 16 are punched into the molded or extruded elastomeric tip 14. The side holes 16 are located on either side of the elastomeric tip 14, whereby all side holes 16 of each side are arranged on an imaginary line parallel to the longitudinal axis of the elastomeric tip 14.

As can be seen in FIG. 3, the side holes 16 have an elongate or longitudinal shape comprising a slot 18 with rounded ends 20. The elongate side holes 16 are inclined between 30 and 60 degrees, preferably 45 degrees, to the imaginary line parallel to the longitudinal axis of the catheter. The distance between the centers of two adjacent side holes is between 0.1 and 0.2 inches and is preferably approximately 0.15 inches.

Each elongate side hole 16 on one side of the catheter is inclined upwardly or downwardly relative to the imaginary line and each opposite side hole on the other side of the catheter is inclined downwardly or upwardly relative to the imaginary line so that opposed side holes 16 form an X.

Figure 2:
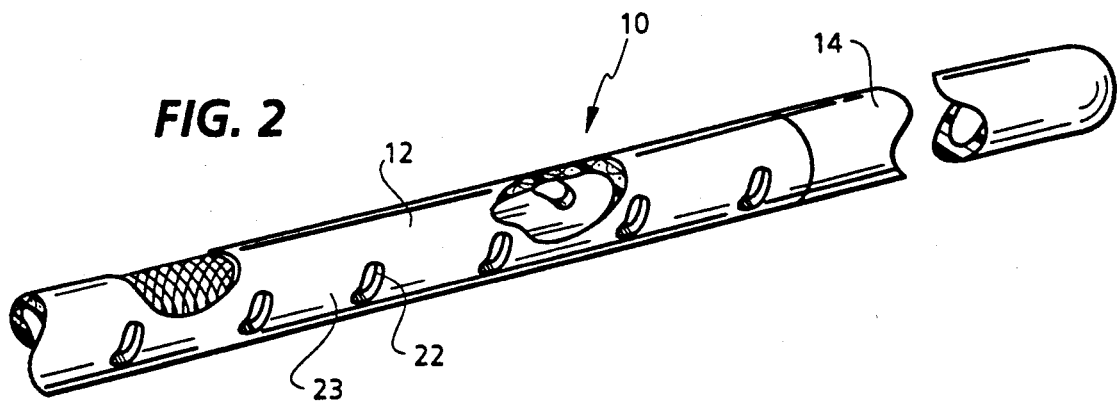
FIG. 2 is a perspective view of the distal end of another catheter similar to the catheter shown in FIG. 1, but showing side holes within a tubular braided body of the catheter.
Figure 4:
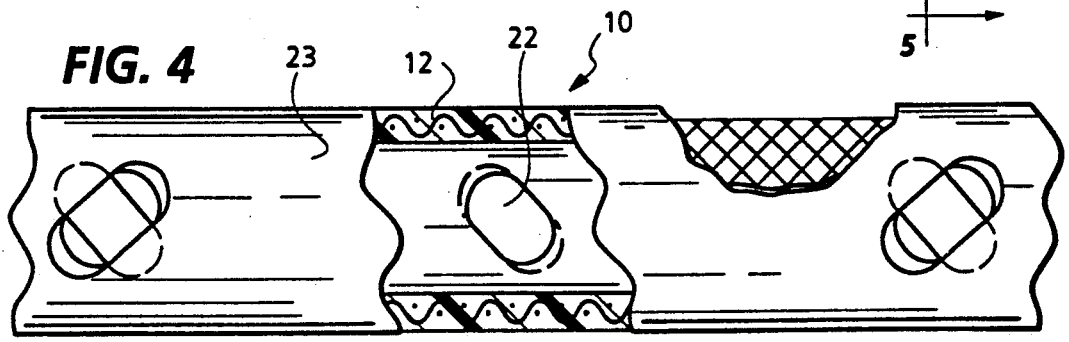
FIG. 4 is a side view of the distal end of the catheter shown in FIG. 2 with parts broken away.

A second embodiment of a catheter constructed according to the teachings of the present invention is shown in FIGS. 2 and 4. Here, elongate side holes 22 are punched into a tubular braided body 23 of the distal end of the catheter. The side holes 22 and their arrangement are identical to the side holes 16 and their arrangement of the first embodiment, as described above.

Figure 6:
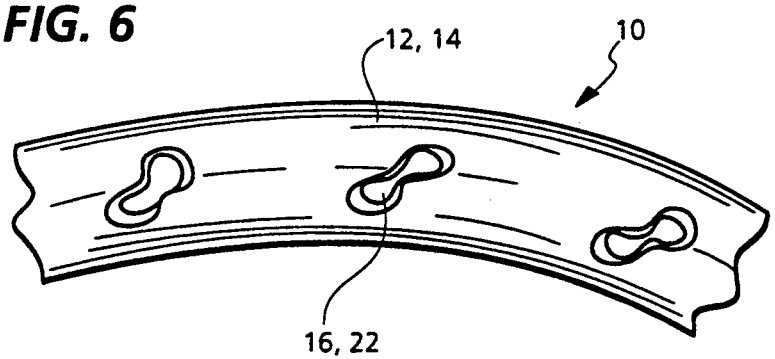
FIG. 6 is a side view of the distal end of the catheter with the distal end in a bent position.

FIG. 6 shows the distal end of the catheter 10 in a bended position. While being bent, the tubular body 12 or the elastomeric tip 14, respectively, is under tension. The inclined side holes 16, 22 act as a buffer to absorb a part of the surface tension. Thereby, the shape of the side holes 16, 22 is distorted, as can be seen in FIG. 6.

Figure 7:
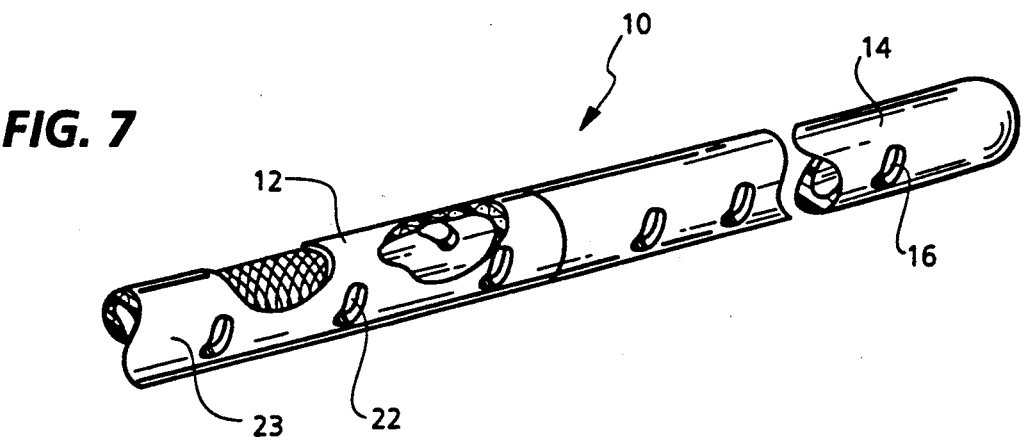
FIG. 7 is a perspective view of a distal end of a catheter with parts broken away similar to the catheters shown in FIGS. 1 and 2, but showing side holes within a tubular braided body and an extruded elastomeric tip of the catheter.

Because the side holes 16, 22 absorb partially the surface tension of the tubular body of the catheter 10 and the remaining tension in the tubular body 12 is decreased. As a result kinking of the catheter 10 is reduced if not altogether eliminated for smooth bent up to 90 degree. A third embodiment of a catheter constructed according to the teachings of the present invention is shown at FIG. 7 wherein elongate side holes 22 and 16 are arranged as previously described, but are located in both tubular braided body 23 and extruded elastomeric tip 14, respectively, of the distal end of catheter 10.

From the foregoing description it will be apparent that the catheter of the present invention provides advantages, particularly reduced kinking, over prior art catheters and that modifications can be made thereto without departing from the teachings of the present invention.

Accordingly the scope of the present invention is only to be limited as necessitated by the accompagning claims.

I claim:

1. A catheter for use in an angioplasty system, said catheter comprising:
    a tubular body with a proximal end, a distal end and a distal end portion having a plurality of holes in and along opposite sides of said distal end portion;
    each hole having an elongate shape and a center axially aligned with the center of a hole on the opposite side of said distal end portion, said centers of said holes being located on an imaginary line parallel to the longitudinal axis of said catheter;
    each elongate hole being inclined not less than 30 degrees and not more than 60 degrees upwardly or downwardly relative to said imaginary line; and
    each elongate hole on one side of said catheter being inclined upwardly or downwardly relative to said imaginary line and each opposite side hole on the other side of said catheter being inclined to the imaginary line at an angle different than the aligned hole on the one side so that each pair of opposed holes form an X.

2. The catheter of claim 1, wherein said holes are elongate slots with rounded ends.

3. The catheter of claim 1, wherein each hole is inclined approximately 45 degrees to said imaginary line.

4. The catheter of claim 1, wherein the distance between the centers of two adjacent holes is between 0.1 and 0.2 inches.

5. The catheter of claim 1, wherein the distance between the center of two adjacent holes is approximately 0.15 inches.

6. The catheter of claim 1, wherein said catheter has a tubular braided body and a molded or extruded elastomeric tip fused thereon.

7. The catheter of claim 6, wherein said holes are located in said tubular braided body.

8. The catheter of claim 6, wherein said holes are located in said extruded elastomeric tip.

9. The catheter of claim 6, wherein said holes are located in said tubular braided body and in said extruded elastomeric tip.

10. A catheter comprising:
    a tubular body having a proximal end, a distal end and a distal end portion having holes located in said distal end portion in and along opposite sides of said distal end portion;
    each hole having an elongate shape, a center axially aligned with the center of a hole on the opposite side of said distal end portion with the centers of said holes being location on an imaginary line parallel to the longitudinal axis of said tubular body and being inclined upwardly or downwardly relative to an imaginary line parallel to the longitudinal axis of said tubular body and the holes on one side being inclined at a different angle to the imaginary line than the holes on the other side such that opposed holes form an X for minimizing kinking of said tubular body when it is bent.

* * * * *